United States Patent
Molaison

(10) Patent No.: US 8,180,651 B2
(45) Date of Patent: May 15, 2012

(54) SYSTEM AND METHOD OF PATIENT DESTINATION PREDICTION

(75) Inventor: Jennifer Lynn Molaison, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 378 days.

(21) Appl. No.: 12/624,932

(22) Filed: Nov. 24, 2009

(65) Prior Publication Data
US 2011/0125514 A1  May 26, 2011

(51) Int. Cl.
G06Q 10/00 (2012.01)
G06Q 50/00 (2012.01)

(52) U.S. Cl. ............................................................ 705/2

(58) Field of Classification Search ........................ None
See application file for complete search history.

(56) References Cited

U.S. PATENT DOCUMENTS

| | | | |
|---|---|---|---|
| 4,706,689 A * | 11/1987 | Man | 600/302 |
| 6,135,970 A | 10/2000 | Kadhiresan et al. | |
| 6,838,992 B2 | 1/2005 | Tenarvitz | |
| 6,847,892 B2 | 1/2005 | Zhou et al. | |
| 6,998,978 B2 | 2/2006 | Kirkeby | |
| 7,091,863 B2 | 8/2006 | Ravet | |
| 7,328,131 B2 | 2/2008 | Donofrio et al. | |
| 2002/0060630 A1 * | 5/2002 | Power | 340/573.1 |
| 2002/0121989 A1 * | 9/2002 | Burns | 340/901 |
| 2007/0021100 A1 * | 1/2007 | Haave et al. | 455/404.2 |
| 2010/0097208 A1 * | 4/2010 | Rosing et al. | 340/539.13 |

* cited by examiner

*Primary Examiner* — Neal Sereboff
(74) *Attorney, Agent, or Firm* — Andrus, Sceales, Starke & Sawall, LLP

(57) ABSTRACT

A system and method of predicting telemetry signal dropout creates a prediction of patient destination. The method includes defining a telemetry coverage area, receiving a location of a monitored patient, recording the received location, calculating a trajectory and speed, and comparing the location, trajectory, and speed of the patient to historical patient movement trends to predict patient destination. The system includes a remote unit worn by a patient and at least one telemetry receiver, a location services computer, a patient location database, a location prediction computer, and a graphical display. The location services computer receives the location information and computes a location, speed, and trajectory of the patient. The location prediction computer compares the computed location, speed, and trajectory of the patient to previously acquired locations, speeds, and trajectories to predict a patient destination.

20 Claims, 3 Drawing Sheets

SYSTEM AND METHOD OF PATIENT DESTINATION PREDICTION

BACKGROUND OF THE INVENTION

The present disclosure is related to the field of telemetry. More specifically, the present disclosure is related to a system and method for predicting the destination of a patient.

Telemetry systems, such as those used in the medical field, are designed to provide continuous physiological monitoring of ambulatory patients. The telemetry system permits ambulatory patients to have the freedom to move around, which has been shown to aid in the recovery process, while being under constant physiological monitoring by either a clinician, an automated monitoring system, or both. The area in which the monitored patients are permitted to move while being monitored is restricted by the areas of the hospital or medical care facility that are designed for, and equipped, with the hardware for telemetry coverage. If a patient moves outside of the telemetry coverage area, continuous monitoring of the patient may lapse, causing delays in treatment should a medical event, such as cardiac arrest, occur during this time. It is also difficult for clinical personnel to locate the patient, when the patient is outside of the telemetry coverage area. The location of a patient within the telemetry coverage area is often determined and/or provided to clinical personnel by location services functionality employed in conjunction with the telemetry system.

Currently available technology provides alerts indicative of telemetry signal dropout that are caused when the patient goes out of the telemetry coverage area. However, by the time that these alerts are presented, monitoring coverage of the patient has already lapsed, and the specific location of the patient is unknown.

BRIEF DISCLOSURE

Therefore, it is desirable to provide clinical personnel with a predictive warning of telemetry signal dropout due to an ambulatory patient leaving a telemetry coverage area.

An embodiment of a method of predicting telemetry signal dropout includes defining a telemetry coverage area by locating a telemetry antenna in the telemetry coverage area. Next, a location of a monitored patient is received with the telemetry antenna. A database records the received patient location over time. A processor calculates a trajectory and speed of the monitored patent from the received location and one or more previously received locations. The processor compares the location, trajectory, and speed of the monitored patient to the patient location, trajectory, and speed information previously recorded in the database. The processor then creates a prediction of patient destination.

An additional embodiment of a method of predicting telemetry signal dropout includes defining a telemetry coverage area. Next, a patient telemetry signal is continuously received. Then a patient location is continuously received. Next a patient trajectory and a patient speed is computed from the received patient location. Then the patient location, patient trajectory, and patient speed are recorded in a database comprising previously recorded patient locations, patient trajectories, and patient speeds. Then the patient location, patient trajectory, and patent speed are compared to the first database to correlate the patient location, patient trajectory, and patient speed to previously recorded patient locations, trajectories, and speeds. Finally, a probability that the patient will leave the telemetry coverage area is calculated.

Also disclosed herein are embodiments of a system for predictive warning of telemetry signal dropout. The system includes a remote unit worn by a patient. The remote unit transmits telemetry information. A plurality of telemetry receivers are distributed throughout a telemetry coverage area. At least one of the plurality of telemetry receivers receives the transmitted telemetry information. A location services manager receives the location signal from the access points and computes the location of the patient, the speed of the patient, and the trajectory of the patient. A patient location database records the computed location, speed, and trajectory of the patient. The patient location database also records location, speed, and trajectory from a plurality of patients in the telemetry coverage area. A location prediction computer compares the computed location, speed, and trajectory of the patient to the locations, speeds, and trajectories stored on the database to predict a patient destination and produces an alarm if the patient destination is outside of the telemetry coverage area. A graphical display receives and presents the patient destination and receives and presents the alarm.

DETAILED DESCRIPTION OF THE INVENTION

Figure 1:
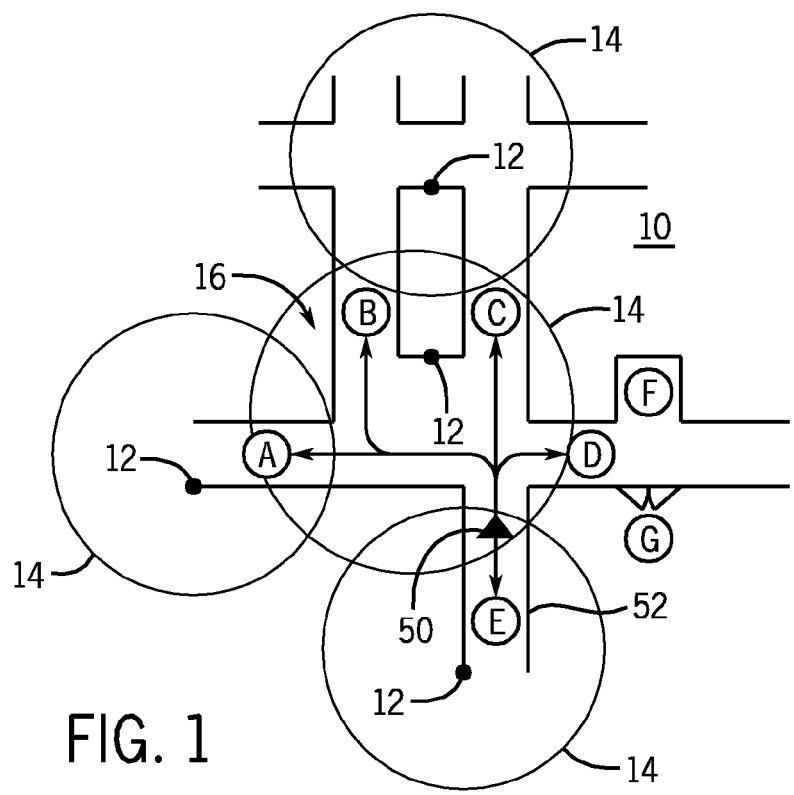
FIG. 1 is a floor plan of a medical care facility with a telemetry coverage area.

FIG. 1 depicts a diagram of a partial floor plan 10 of a medical care facility. While the floor plan 10 used in the present disclosure is that of a medical care facility, it is understood that the present disclosure is not limited in geography to only medical care facilities, but may be any type of facility within which telemetry monitoring is implemented. These facilities may include a medical care facility such as a hospital or clinic, but may also include any other facilities implementing a telemetry system, including, but not limited to nursing homes, assisted living centers, or schools; however, for the present disclosure the example of a medical care facility is used. The medical care facility includes a plurality of antennas 12 or other signal receiving devices that receive broadcasted telemetry signals from a remote unit (not depicted) worn by, or otherwise associated with, a patient or monitored subject 50.

The receiving range 14 of each of the plurality of antennas 12 defines a telemetry coverage area 16. The receiving range 14 of each of the antennas 12 may be controlled or adjusted based on the antenna receiving strength or the transmission strength of the signals from the remote units. In an example, the same receiving range 14 may be achieved through the use of stronger antennas 12 and weaker transmission remote units as may be achieved through the use of weaker antennas 12 and stronger transmitting remote units. Within the telemetry coverage area 16, one or more of the antennas 12 receives a telemetry signal broadcasted by the remote unit (not depicted) associated with each of the patients. This telemetry signal may include measured physiological data, physiological data that is derived from the measured physiological data, or patient communications, such as patient initiated alarms or patient subjective physical assessments.

The remote unit transmits a location signal that is used to identify the location of the patient within the medical care facility. The location signal may be one that is detected by one or more of the antennas 12, in order to triangulate the remote unit associated with the patient. In an embodiment, at least three antennas receive a location signal for triangulation of the patient location; however, this is not limiting on the number of antennas 12 distributed through the telemetry coverage area 16 or the overlap of the receiving ranges 14 of the plurality of antennas 12. Alternatively, the location signal may include information indicative of the location of the patient, such as positional coordinates as determined by a GPS system within the remote unit. Therefore, the location signal may either be indicative of the actual patient location, or may be a signal that is used to derive the location of the patient within the telemetry coverage area 16.

The telemetry coverage area 16 is defined by one or more antennas 12 which may be located on multiple floors within a medical care facility. As noted above, the telemetry coverage area 16 may have antennas 12 distributed to ensure overlap of the receiving ranges of multiple antennas 12, which aids in patient triangulation.

Figure 2:
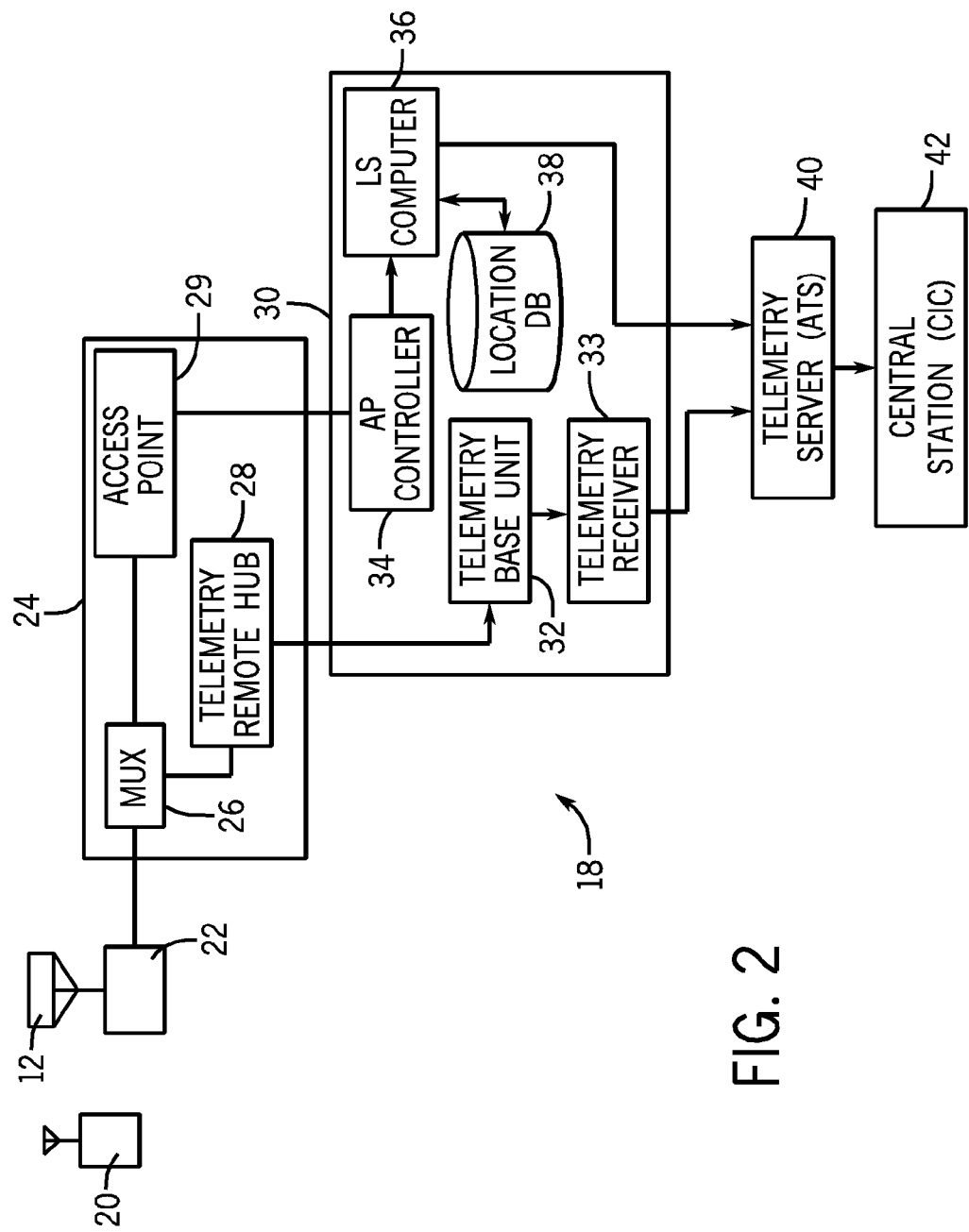
FIG. 2 is a system diagram of a telemetry system.

FIG. 2 is a schematic diagram of a telemetry system 18 that may be implemented in a medical care facility. The telemetry system 18 includes the electrical hardware, software, and firmware components that operate the telemetry system 18. A remote unit 20 is worn by, attached to, or otherwise associated with each of the patients (not depicted) that are being telemetrically monitored. The remote unit 20 transmits one or more signals that include telemetry and/or location information. These signals are received by the antenna 12, of which a plurality are distributed throughout the medical care facility to define the telemetry coverage area 16 (shown in FIG. 1). However, for the sake of simplicity in FIG. 2, only a single antenna 12 is shown. Each antenna 12 is associated with an amplifier 22 that amplifies the signal received from the remote unit 20. Although not depicted, the amplifier 22 may also include other forms of signal conditioning or processing, including, but not limited to, filtering and/or digitization.

The signals from the amplifier 22 are transmitted to a remote closet 24. The remote closet 24 collects all of the signals received by the plurality of antennas 12 in a defined area of the telemetry coverage area 16. In one example, the medical care facility includes a telemetry coverage area 16 that expands to multiple floors of the medical care facility. In such an example, a remote closet 24 may be placed at each of the floors in order to collect and process the signals received by the antennas 12 on that floor. The remote closet 24 includes a multiplexer 26 that handles the transmission of the telemetry and location information for a plurality of remote units 20 transmitting to the remove closet 24. The multiplexer 26 separates the lower frequency telemetry signals from the higher frequency location signals and directs the received signals for further processing. While the telemetry system 18 depicted in FIG. 1 is a system that places the telemetry and location information on the same antenna 12, this is not required, and instead of using the multiplexer 26, separate antenna systems may be implemented to separately obtain the telemetry and location signals.

From the multiplexer 26, the telemetry information is provided to a telemetry remote hub 28 that prepares the telemetry information for transmission from the remote closet 24 to the main closet 30 that collects all of the information from the remote closets 24 distributed throughout the telemetry system 18. The main closet 30 is centrally or otherwise conveniently located to receive the telemetry and location information from all of the remote closets 24 in the system 18. The telemetry remote hub 28 may transmit the telemetry information to a telemetry base unit 32 in the main closet 30 that receives and processes the telemetry information. In an embodiment, the transmission of telemetry information from the telemetry remote hub 28 to the telemetry base unit 32 is performed by fiber optic transmission technology and the telemetry remote hub 28 and the telemetry base unit 32 perform the signal conditioning required for the optical fiber conversion necessary for the transmission.

After the telemetry information is transmitted from the telemetry remote hub 28 to the telemetry base unit 32, the telemetry base unit 32 processes the fiber optic signal to extract the telemetry information embedded thereon. The telemetry base unit 23 sends the telemetry information to a telemetry receiver 33 that receives the telemetry information and further directs the telemetry information to the telemetry server 40.

In the remote closet 24, the separated location signals from the multiplexer 26 are provided to an access point 29. The access point 29 measures the strength of the location signal from the base unit 20 received by one or more antenna 12. In a telemetry system 18 wherein a plurality of antennas 12 are distributed throughout the telemetry coverage area, the signal strengths determined by the access point 29 can be used to triangulate the remote unit 20 as the varying signal strength from a plurality of antennas 12 may be used to determine the patient location with reference to each of the antennas receiving the location signal.

The access point 29 of the remote closet 24 provides the location information, including the received signal strengths to the main closet 30 through any number of information transmission technologies, including wire, wireless, or fiber optic technologies. An access point (AP) controller 34 is connected to each of the access points 29 if a plurality of remote closets 24 exist in the telemetry system 18. The AP controller 34 coordinates the transmission and reception of the location information from the access points 29 of each of the remote closets 24.

The location information is provided from the AP control 34 to a location services (LS) computer 36. The LS computer includes computer readable code stored on a computer readable medium (not depicted) that embodies software as detailed further herein for calculating location information regarding a patient. Software implemented by the LS computer 36 may also include software required to operate an advanced neural network (ANN), as disclosed in embodiments herein.

The LS computer 36 is further connected to a location database 38 that stores the location information from the LS computer 36 for later retrieval and reference by the software operating on the LS computer 36 in determining patient location information.

The main closet 30 transmits both the telemetry information and the location information to a telemetry server 40 that coordinates the telemetry and location information with other patient, facility, and services information that is required for the operation of other features of the telemetry system 18 that are not central to the present disclosure. Such additional telemetry system functionalities include patient medical history and electronic medical record (EMR) access, clinical staff information, medical care facility availability, and facility capacity.

The telemetry server 40 may also perform analysis of the received telemetry information, such as to process measured physiological data, derive additional physiological data from the measured physiological data, and/or apply institutional diagnostic rules such as to perform automatic or automated diagnostic tests. The telemetry server 40 transmits all of the telemetry information, and location information to the central station 42. The central station 42 may otherwise be known as the telemetry command center, or "war room." The central station 42 is where one or more clinical staff are presented with the telemetry and location information for all of the patients currently under monitoring in the telemetry system. The telemetry information is presented to the clinical staff such that the clinical staff can remotely monitor the physiological condition of the telemetrically monitored patients depending upon changes in the monitored physiological condition of the remotely located patients, the clinical staff may electronically update a patient's diagnosis or treatment regimen, or may initiate intervention by other clinical staff with the patient. In the event that physiological conditions indicate one or more alarm conditions, the clinical staff at the central station 42 may evaluate the alarm conditions and initiate the proper response based upon those conditions.

While the above description of the telemetry system 18 has been made with respect to a large number of hardware components that operate software or firmware in order to form the functionality, data processing, and communication as disclosed above, it is understood to one of ordinary skill in the art that depending on the specific implementation of the telemetry system 18 individual components described herein may be combined into a single piece of hardware or may be implemented as a smaller module of a larger control system software. Additionally, one of ordinary skill in the art would also recognize that the communication aspects disclosed herein are merely an exemplary embodiment and that the communication and data transmission would be modified to the specific needs of the telemetry system 18 implemented within a medical care facility.

The telemetry system 18 can provide a cost effective and convenient way to monitor ambulatory patients. This benefits the patients as the ability of a recovering patient to move about the patient's surroundings has been found to aid in recovery times; however, while patients are recovering from illness or a medical procedure, they are at increased risk of being afflicted by a severe medical condition. Examples of severe medical conditions include a heart attack or stroke. Thus, these ambulatory patients still require constant monitoring. A problem arises if a telemetrically monitored patient moves outside of the telemetry coverage area 16 (FIG. 1), the telemetry system 18 both no longer receives the critical physiological data required to continuously monitor the patient, but also the location of the patient becomes unknown, putting the patient at risk of delayed clinician intervention or treatment, should the patient develop a serious medical condition.

Therefore, as disclosed further herein, the LS computer 36 may provide with the location information, a prediction if an ambulatory patient will move out of the telemetry coverage area 16, thus causing telemetry signal dropout. Alternatively, the prediction of patient destination may be created using a separate location prediction computer (not depicted).

Referring back to FIG. 1, the floor plan 10 of FIG. 1 is also representative of an embodiment of the information displayed by a graphical display of the central station 42. The central station 42 may present the patient location information graphically, such as using a floor plan representation, like FIG. 1, that indicates both the monitored patients and their potential destinations. Alternatively, the central station 42 may present the patient location information and destination predictions in tabulative or textual formats. In still further embodiments, the destination prediction may only be presented as an alarm, when it is predicted that the probability of the patient leaving the telemetry coverage area 16 meets a predetermined threshold probability.

In FIG. 1, a patient 50 is indicated by a graphical representation, such as an arrow, the arrow graphically represents both the location of the patient 50 within the floor plan 10 and also indicates the patient's direction of travel. In alternative embodiments, it is understood that additional indications of other telemetrically monitored patients may be made on the same display. Additionally, the patient speed may be indicated such as through the use of a tail (not depicted) or progressively fading indication of the patient 50 location at previous time intervals, such as two second intervals or one second intervals.

As noted with respect to FIG. 2, a remote unit 20 is associated with the patient 50. The remote unit 20 transmits its location information as picked up by one or more of the antennas 12 in the telemetry coverage area 16. By monitoring this patient location information, the LS computer 36 can compute the patient's location within the telemetry coverage area 16, the speed that the patient is traveling, and the trajectory of the patient, or the direction the patient is traveling. The LS computer 36 records this information in a location database 38 for each of a plurality of monitored patients in the telemetry coverage area 16. The data in a location database 38 includes not only current patients within the telemetry coverage area, but the location database 38 also stores the location information for previously telemetrically monitored patients in the telemetry coverage area 16.

Computer 36 uses the previously recorded patient location information in the location database 38 to identify the instance rates of patients moving from a current location to a variety of destinations. These instance rates or probabilities may then be further detailed using artificial intelligence techniques such as artificial neural networks (ANN) or fuzzy logic in order to correlate not only the patient location, but the calculated patient trajectory and speed to the previously recorded patient location information. ANN or fuzzy logic implementations may be used to computer historical patient movement trends throughout the telemetry coverage area 16. This allows for the destination predictions to be correlated to the location information presently received and computed for the monitored patient. Therefore, the present telemetry system 18 provides improved prediction of patient destination using both currently measured and computed patient location information with historical patient movement trends obtained from the historical location information of other patients and/or the monitored patient in the same telemetry coverage area 16.

As noted above, the floor plan 10 of FIG. 1 may represent an embodiment of the information presented by the central station 42. In this example, a patient 50 is indicated as moving through the telemetry coverage area 16 in a hallway 52. The location information transmitted by the remote unit 20 associated with the patient 50 received by the telemetry system 18 is used to determine the location, speed, and trajectory of the patient 50. The LS computer 36 records the patient's actual location and path in the location database 38 for reference in future destination determinations. The LS computer 36 also performs a current destination prediction. In this destination prediction, the LS computer 36 identifies by analyzing previous destinations of patients in the same telemetry coverage area 16 to determine historical patient movement trends and comprising these historical patient movement trends to the current received/measured/calculated location, trajectory, and speed of the patient 50. In this example, the LS computer 36 identifies that there are five potential destinations of the patient 50. These potential destinations are indicated on the floor plan 10 as destinations A, B, C, D, and E.

The LS computer 36 further determinates a probability that the patient 50 will go to each of these destinations.

As an example, the LS computer 36 may determine, based on the historical patient movement trends and the current location, trajectory, and speed of the patient 50, that the following probabilities exist that the patient will move to each of the identified destinations:

| DESTINATION | PROBABILITY % |
|---|---|
| A | 60% |
| B | 22% |
| C | 8% |
| D | 4% |
| E | 6% |

Thus from the exemplary Table above, it can be determined that the patient 50 has a 94% probability of moving forward. The patient 50 also has a 60% probability of moving to destination A, while only having a 22% probability of moving outside of the telemetry coverage area 16, to designated destination D. Therefore, the patient 50 at the specified location, speed, and trajectory will be regarded as a 22% risk for telemetry signal dropout based upon the patient leaving the telemetry coverage area 16 at destination D.

The medical care facility may define its own alarm definitions for telemetry signal dropout risk as well as define the responses that are initiated by clinical staff at the central station 42 upon the meeting of these predefined probability criteria. Some institutions may be highly risk adverse and therefore would desire to intervene any time the destination probability of the destination outside the telemetry coverage area 16 crosses a minimal threshold percentage. This threshold percentage may be relatively low, such as 10-20% likelihood, or lower, based at the discretion of the medical care facility. Alternatively, a progression of patient interactions may escalate as the probability that the patient will leave the telemetry coverage area 16 increases. These intervention escalations may begin with a page or other audible or textual alert that is sent to the remote unit 20 associated with the patient 50. This may be escalated to the dispatch of clinical staff to the location of the patient 50 or to the patient's predicted destination in order to intercept the patient 50 before the patient 50 leaves the telemetry coverage area 16. It is further understood that in alternative embodiments some or all of these responses may be automated or automatically initiated responses and do not require clinician action in order to initiate or carry out.

The LS computer 36 (FIG. 2) may simplify the destination prediction by dividing the telemetry coverage area 16 into a plurality of destination areas. Therefore, the LS computer 36 may more easily define historical patient movement trends through ANN or fuzzy logic techniques. These or other data processing techniques may be used to process the large amount of stored patient location information. The division of the telemetry coverage area 16 into discrete destinations (A, B, C, D, E) help to identify a probability that the patient will enter one of these destinations.

Figure 3:
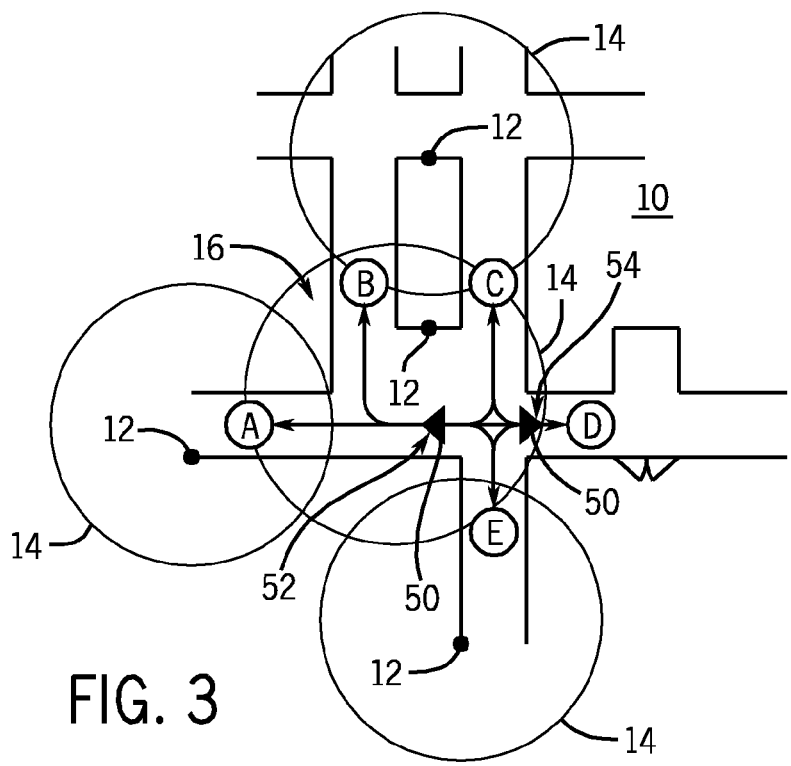
FIG. 3 is another floor plan of a medical care facility.

Referring now to FIG. 3, it depicts the floor plan 10 with two different alternative locations, location 52 and location 54, for the patient 50 to proceed from the location in FIG. 1. From both locations 52 and 54, the patient 50 may move to the same five destinations A, B, C, D, and E. If the patient 50 moves to location 52, as the patient 50 moves, the LS computer 36 continuously updates the destination prediction, taking into account the updated patient location, trajectory, and speed, as well as the historical patient movement trends stored in the location database 38. In the present example, by the time the patient 50 moves to location 52, the destination probabilities have changed to:

| DESTINATION | PROBABILITY % |
|---|---|
| A | 59% |
| B | 35% |
| C | 2% |
| D | 2% |
| E | 2% |

By referencing the above Table, it can be seen that as the patient 50 turned in the direction away from the telemetry coverage area 16 boundary and destination D, the probability that the patient would enter this destination is drastically reduced. The reduction in this destination probability of the destination D would be due to the fact that patients historically at location 52 on the trajectory and speed of patient 50, rarely turn around and head out of the telemetry coverage zone 16 to destination D.

However, in an alternative example, if the patient 50 moves from location in FIG. 1 to location 54 depicted in FIG. 2, then as the patient moves between those two locations, the LS computer 36 will compute the new destination probabilities, such that by the time the patient 50 reaches location 54, the destination probabilities are:

| DESTINATION | PROBABILITY % |
|---|---|
| A | 5% |
| B | 5% |
| C | 5% |
| D | 80% |
| E | 5% |

By reference to the above Table, it can be seen that by the time the patient 50 reaches location 54, it becomes very likely that the patient 50 will leave the telemetry coverage area 16 and move to destination D. This escalation of the probability that the patient's telemetry signal will be lost due to moving out of the telemetry coverage area 16, may trigger an appropriate response from the clinical staff at the central station 42. The clinical staff at central station 42 would dispatch clinical staff to location 54 or destination D in an attempt to first intercept the patient 50 before the patient leaves the telemetry coverage area 16, or if the clinical staff response arrives too late, the patient 50 is recovered at or near destination D with minimal telemetry signal dropout.

Referring back to FIG. 1, if the patient 50 moves to destination D, both the patient's telemetry signal and location signal would be lost. The patient would no longer appear on the floor plan 10. In this instance, the LS computer 36 saves the patient location, trajectory, and speed at the time of the telemetry and location signal dropout. In an additional functionality of the LS computer 36, the LS computer 36 uses patient location information stored in the location database 38 to additionally predict a destination outside of the telemetry coverage area 16 that the patient 50 may be most likely to be found.

The patient location information used to determine probability of patient location outside of the telemetry coverage area 16 may be based upon reporting by clinical staff that find telemetry patients outside of the telemetry coverage area 16. The reporting of clinical staff may be analyzed and compiled in order to determine probabilities of where patients leaving the telemetry coverage area 16 may be headed after signal dropout occurs.

In FIG. 1, locations F and G represent two locations outside of the telemetry coverage area 16 that may be deemed as likely patient destinations outside of the telemetry coverage area 16. Locations F and G may be specific destinations of patients leaving the telemetry coverage area 16 due to features about these locations. For example, location F may be the site of a point of interest such as vending machines, or a fish tank that attract patients, while location G may be an outdoor park or sitting area.

The LS computer 36 computes a probability determination for the likelihood that the patient leaving the telemetry coverage area 16 may be found at one of locations F or G. This probability may be similar to that previously calculated with respect to patient destination predictions. The calculated probability is transmitted to the central station 42 to be presented on a graphical display. Thus, if the patient 50 leaves the telemetry coverage area 16, the graphical display of the central station 42 may present an indication that there is a 25% likelihood that the patient 50 is at destination F while there is a 50% probability that the patient 50 is at destination G. The probabilities provided in this determination may or may not add up to 100% due to rounding, or the consideration of other locations. For the sake of simplicity, in some embodiments, only those locations that are above a predetermined probability threshold are presented as likely options. Alternatively, the system could present all the calculated probabilities.

It is to be understood that the effectiveness of this type of location prediction outside of the telemetry coverage area 16 may be dependent upon a clinical staff reporting system, whereby the patient location information is collected that is indicative of where the clinical staff actually locate the patient 50 outside of the telemetry coverage area 16. This type of reporting identifies the locations outside of the telemetry coverage area 16 where the patients are likely to go after telemetry signal dropout.

In an additional aspect, the location database 38 keeps track of all interventions on patient movement. Often, these are recorded by clinical staff after intervening on patient movement. If left unreported or unaccounted for, these interventions may skew the probabilities of the patients leaving the telemetry coverage area 16, such as to under report the actual instance of patient signal dropout, in instances where no intervention is initiated. Therefore, the LS computer 36 may credit an interaction as full or partial consideration that the patient left the telemetry coverage area.

With respect to FIG. 1, in a still further embodiment, an exemplary table of destination probabilities presented by the central station 42 is:

| DESTINATION | PROBABILITY % |
|---|---|
| A | 60% |
| B | 22% |
| C | 8% |
| D | 4% |
| E | 6% |

Referring to the table above, based upon the location, trajectory, and speed of the patient 50, and historical patient movement trends, the LS computer 36 may compute that the patient 50 is relatively unlikely to leave the telemetry coverage area 16 to go to destination D. In this instance, the patient 50 is likely to pass very close to the edge of the telemetry coverage area 16 and there is a potential for the patient to leave the telemetry coverage area 16 resulting in telemetry signal dropout. However, based upon the historical patient movement trends and the monitored patient location, trajectory, and speed, the LS computer 36 indicates to the clinical staff at the central station 42 a low probability that the patient will leave the telemetry coverage area 16. Therefore, no intervention, or a low intervention, may be initiated, thus conserving resources and not interrupting the ambulatory movement of the patient 50 or the current tasks being performed by clinicians.

In embodiments of the telemetry system 18, the LS computer 36 may further be communicatively coupled to a database of patient demographic information (not depicted), or alternatively, the location database 38 may also include patient demographic information that may be further used to increase the accuracy of the destination predictions of the telemetry system 18. The stored demographic information may correlate the patient's age, gender, or ethnicity with particular historical patient movement trends or behavior patterns. In one such example, referring to FIG. 1, if the patient 50 leaves the telemetry coverage area 16 by moving to destination D, if destination F represents a fish tank and destination G represents a sitting area or park, the LS computer 36 may determine that there is a correlation that patients below a certain age are more likely to go to location F, presumably to view the fish in the fish tank while patients above a certain age are move likely to be found at the sitting area G.

In a still further embodiment of the telemetry system 18, the location database 38 may also store the historical movement trends for each individual patient 50 separately from the group of all patients as a whole. Thus, the LS computer 36 may use the specific movement history of each patient in order to more accurately predict where that patient is going. This additional personalized movement trend determination may help to reduce false positives, resulting in fewer interventions or intervention escalations, requiring the medical care facility resources and staff time. One such example of a personalized patient historical movement trend would be that if patient 50 every morning goes to location B for a particular treatment, therapy, or to visit another particular patient. Despite the fact that the historical patient movement trends on a whole may indicate that a generic patient at the patient's 50 location, trajectory, and speed is likely to leave the telemetry coverage area 16 and move to destination D, the probability of this particular patient 50 following that movement path is comparatively low. Alternatively, the additional personalized movement trend determination may help to proactively warn clinicians of patients at greater risk of leaving the telemetry coverage area 16 than the general patient population.

Figure 4:
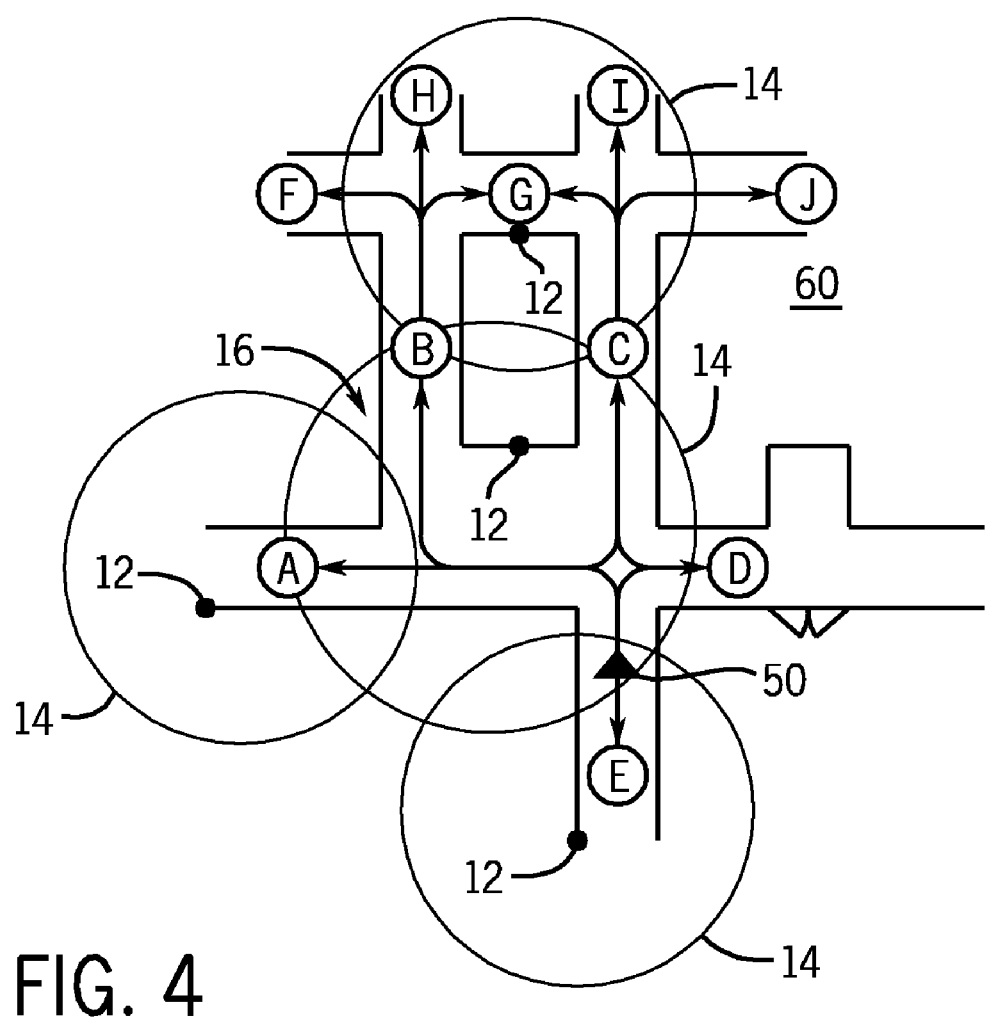
FIG. 4 is a further floor plan of a medical care facility.

Referring now to FIG. 4, FIG. 4 depicts a floor plan 60 that is similar to the other figures, but depicts an alternative potential display presented by the central station 42. If the destination predictions are presented by the central station 42 as merely numerical, textual or escalatory results, then the floor plan 60 of FIG. 4 is a pictorial representation of the logic that may be used by the LS computer 36 in this embodiment. The floor plan 60 of FIG. 4 is different from that depicted in FIG. 1 in that the floor plan 10 of FIG. 1 depicted only the nearest extrapolation of potential patient destination. Therefore, in the embodiment of FIG. 1, the predictive capability of these destination predictions are limited to a next destination of the patient. However, additional warning time of potential telemetry signal dropout beyond a simple "next destination" may be provided in some embodiments. Therefore, in the floor plan 60 of FIG. 4, additional destinations F-J are included in the floor plan 60. These additional destinations extend from destination B and C in the original floor plan 10. Thus, the probability that the patient moves to any of destination F-J, would first require that the patient move through destination B or C. Therefore, the probabilities of destinations F-J are a subset of the probability that the patient move to destinations B or C.

In an embodiment of this patient destination prediction scheme, the destination probabilities may appear at:

| DESTINATION | PROBABILITY % |
|---|---|
| A | 47% |
| B | 22% |
| C | 20% |
| D | 5% |
| E | 6% |
| F | 12% |
| G | 8% |
| H | 7% |
| I | 5% |
| J | 10% |

A feature of the embodiment of floor plan 60 is apparent from this example in that it may be noted that the patient 50 has a greater probability of leaving the telemetry coverage area 16 at destination J, causing telemetry and location signal dropout, than the much closer destination D. Thus, clinical staff at the central station 42 are provided with a warning of a possibly counter intuitive destination prediction and may monitor the location of the patient 50 more closely, or provide the necessary intervention, or intervention escalation with respect to the more probable destination causing signal dropout.

As stated previously, the embodiments of the floor plan 10, 60 are merely exemplary as to the type of graphical presentation that may be made by the central station 42 to clinical staff. Alternative to the graphical depiction of these figures, graphical indications that only focus on the possible patient point of departure from the telemetry coverage area 16 may be implemented. These embodiments may only track the location, speed, and trajectory of the patient 50, while noting only those paths and probabilities that lead to telemetry signal dropout. Alternatively, rather than specific patient vectors and discrete destination locations, a scatter plot or heat map or other type of graphical representation of probability may be used to graphically depict the likelihood that the patient 50 would move to a particular destination.

Finally, as mentioned above, the central station 42 may rather present the destination predictions in a more simplistic numeral or textural form such, as in the non-limiting example, the tables presented above, or may only be presented to the clinical staff at the central station 42 only upon meeting one or more probability thresholds for clinical staff intervention, or intervention escalation.

This written description uses examples to disclose various embodiments, including the best mode, and also to enable any person skilled in the art to make and use these embodiments. The patentable scope is defined by the claims may extend to include other examples not explicitly listed that occur to those skilled in the art. Such other examples are intended to be within the scope of the claims if they have structural elements that do not differ from the literal language of the claims, or if they include equivalent elements with insubstantial differences from the literal languages of the claims.

Various alternatives and embodiments are contemplated as being with in the scope of the following claims, particularly pointing out and distinctly claiming the subject matter of the present disclosure.

I claim:

1. A method of predicting patient destination, the method comprising:
   defining a telemetry coverage area with at least one antenna;
   deriving a location of a monitored patient from a signal received by the at least one antenna;
   recording over time the derived location in a database;
   calculating, with a processor operating as a location services computer, a patient trajectory and speed of the monitored patient from the derived location and a previously received location;
   comparing, with the location services computer, the location, trajectory, and speed of the monitored patient to historical patient movement trends recorded in the database;
   creating, with the processor, a prediction of patient destination;
   determining whether the prediction of patient destination is a destination outside of the telemetry coverage area or a change from an expected route; and
   transmitting a notification of the determination.

2. The method of claim 1, further comprising presenting the prediction of patient destination on a graphical display.

3. The method of claim 2 wherein the prediction of patient destination is presented as a probability of a specified patient destination.

4. The method of claim 3 wherein the prediction of patient destination is presented as a probability for each of a plurality of specified patient destinations.

5. The method of claim 3, further comprising:
   defining a specified patient destination of the plurality as outside the telemetry coverage area;
   defining a probability indicative of an alarm;
   initiating the alarm if the probability that the patient destination is a destination outside of the telemetry coverage area meets the probability indicative of an alarm.

6. The method of claim 3, wherein if no location of a monitored patient is received, the method further comprises:
   defining the location of the monitored patient as the last received location of the monitored patient; and
   comparing the last received location, calculated trajectory, and calculated speed, to location information from the database, the location information indicative of a destination outside of the telemetry coverage area; and
   creating a prediction of a patient destination outside of the telemetry coverage area.

7. The method of claim 6, further comprising:
   dispatching a clinician to the predicted patient destination outside of the telemetry coverage area;
   recovering the monitored patient at an actual destination outside of the telemetry coverage area; and
   recording the actual destination outside of the telemetry coverage area as location information in the database.

8. The method of claim 1 wherein the historical patient movement trends are derived from location, trajectory, and speed from a plurality of patients.

9. The method of claim 8, further comprising:
   recording location, trajectory, and speed for a plurality of patients;
   using the recorded location, trajectory, and speed from the plurality of patients to predict the destination of the monitored patient.

10. The method of claim 9, wherein the recorded location, trajectory, and speed comprises previously recorded values of location, trajectory, and speed for the monitored patient.

11. The method of claim 9, further comprising:
dividing the telemetry coverage area into a plurality of destination regions; and
predicting probability that the monitored patient will enter each of the destination regions.

12. A method of predicting a destination of a patient, the method comprising:
defining a telemetry coverage area comprising at least one antenna;
continuously receiving a patient telemetry signal with at least one antenna of the telemetry coverage area;
continuously receiving a patient location signal with at least one antenna of the telemetry coverage area;
deriving a patient location from the received patient location signal;
computing, with a processor, a patient trajectory and a patient speed from the derived patient location;
recording the patient location, patient trajectory, and patient speed in a database comprising previously recorded patient locations, patient trajectories, and patient speeds;
comparing the patient location, patient trajectory, and patient speed to the first database to correlate the patient location, patient trajectory, and patient speed to previously recorded patient locations, trajectories, and speeds; and
calculating, with the processor, a probability that the patient will move to a specified destination; and
transmitting a notification of the calculated probability.

13. The method of claim 12, wherein the previously recorded patient locations, patient trajectories, and patient speeds are recorded from a plurality of patients in the telemetry coverage area.

14. The method of claim 13, wherein the previously recorded patient locations, patient trajectories, and patient speeds comprise those previously recorded from the patient.

15. The method of claim 14, wherein in the comparison of the patient location, trajectory, and speed to the previously recorded patient locations, trajectories, and speeds weights the patient's own previously recorded patient locations, trajectories, and speeds over those of the plurality of patients.

16. A system for predictive warning of telemetry signal dropout, the system comprising:
a remote unit worn by a patient, the remote unit transmits location information and telemetry information;
a plurality of telemetry receivers in a telemetry coverage area that receive the transmitted location information and telemetry information;
a location services computer that receives the location information and computes the location of the patient, the speed of the patient, and the trajectory of the patient;
a patient location database that records the computed location, speed, and trajectory of the patient, and records location, speed, and trajectory from a plurality of patients in the telemetry coverage area;
a location prediction computer comprising software that compares the computed location, speed, and trajectory of the patient to the locations, speeds, and trajectories stored on the database to predict a patient destination, that determines whether the prediction of patient destination is a destination outside of the telemetry coverage area or a change from an expected route, and that notifies the calculated probability; and
a graphical display that receives and presents the patient destination and receives and presents the notification.

17. The system of claim 16 wherein the location prediction computer includes an artificial neural network.

18. The system of claim 17 wherein the telemetry coverage area is defined in the location prediction computer as a plurality of discrete destinations and the predicted patient destination is a probability that the patient will enter a specific destination of the plurality.

19. The system of claim 18 wherein the predicted patient destination is a probability that the patient will enter each of the plurality of discrete destinations.

20. The system of claim 19 wherein the predicted patient destination is a probability that the patient will enter each of the destinations adjacent a patient's current destination.

* * * * *